(12) United States Patent
McGuckin, Jr. et al.

(10) Patent No.: US 7,261,722 B2
(45) Date of Patent: Aug. 28, 2007

(54) APPARATUS AND METHOD FOR TREATING GASTROESOPHAGEAL REFLUX DISEASE

(75) Inventors: James F. McGuckin, Jr., Radnor, PA (US); Peter W. J. Hinchliffe, Campbell Hall, NY (US)

(73) Assignee: Rex Medical, L.P., Conshohocken, PA (US)

( * ) Notice: Subject to any disclaimer, the term of this patent is extended or adjusted under 35 U.S.C. 154(b) by 542 days.

(21) Appl. No.: 10/314,722

(22) Filed: Dec. 9, 2002

(65) Prior Publication Data

US 2003/0120289 A1   Jun. 26, 2003

Related U.S. Application Data

(60) Provisional application No. 60/342,540, filed on Dec. 20, 2001.

(51) Int. Cl.
*A61B 17/10* (2006.01)

(52) U.S. Cl. .................. 606/139; 128/898; 606/144

(58) Field of Classification Search ........... 606/139, 606/144, 213, 148, 151, 153; 623/23.65; 600/29, 106, 104, 107, 153; 128/898; 227/179.01, 227/180.01
See application file for complete search history.

(56) References Cited

U.S. PATENT DOCUMENTS

| 5,037,021 | A | * | 8/1991 | Mills et al. ............... 227/175.1 |
|---|---|---|---|---|
| 5,100,419 | A | | 3/1992 | Ehlers |
| 5,156,614 | A | | 10/1992 | Green et al. |
| 5,188,638 | A | | 2/1993 | Tzakis |
| 5,197,649 | A | | 3/1993 | Bessler et al. |
| 5,271,543 | A | | 12/1993 | Grant et al. |
| 5,330,486 | A | | 7/1994 | Wilk |
| 5,344,059 | A | | 9/1994 | Green et al. |
| 5,355,897 | A | | 10/1994 | Pietrafitta et al. |
| 5,403,326 | A | | 4/1995 | Harrison et al. |
| 5,411,508 | A | | 5/1995 | Bessler et al. |
| 5,431,323 | A | | 7/1995 | Smith et al. |
| 5,571,116 | A | | 11/1996 | Bolanos et al. |
| 5,868,760 | A | | 2/1999 | McGuckin, Jr. et al. |
| 5,947,983 | A | * | 9/1999 | Solar et al. ................. 606/144 |
| 6,048,351 | A | | 4/2000 | Gordon et al. |
| 6,113,611 | A | | 9/2000 | Allen et al. |
| 6,119,913 | A | | 9/2000 | Adams et al. |
| 6,126,058 | A | | 10/2000 | Adams et al. |
| 6,312,437 | B1 | | 11/2001 | Kortenbach |
| 6,338,737 | B1 | | 1/2002 | Toledano |
| 6,358,197 | B1 | * | 3/2002 | Silverman et al. ............ 600/29 |
| 6,383,198 | B1 | | 5/2002 | Hamilton |
| 6,398,795 | B1 | * | 6/2002 | McAlister et al. .......... 606/139 |
| 6,450,390 | B2 | | 9/2002 | Heck |
| 6,544,271 | B1 | | 4/2003 | Adams et al. |

(Continued)

FOREIGN PATENT DOCUMENTS

EP   0442588   8/1991

(Continued)

*Primary Examiner*—Anh Tuan Nguyen
*Assistant Examiner*—Tuan Van Nguyen

(57) ABSTRACT

A minimally invasive surgical procedure is disclosed which includes the steps forming a fold of tissue, extending one or more needles through the fold of tissue, deploying a tissue fastener from an interior lumen of each of the needles, and retracting each of the needles from the fold of tissue such that the tissue fasteners remain deployed in the fold of tissue.

12 Claims, 9 Drawing Sheets

U.S. PATENT DOCUMENTS

| | | |
|---|---|---|
| 6,592,596 B1 | 7/2003 | Geitz |
| 6,601,749 B2 | 8/2003 | Sullivan et al. |
| 6,605,078 B2 | 8/2003 | Adams |
| 6,629,630 B2 | 10/2003 | Adams |
| 6,632,227 B2 | 10/2003 | Adams |
| 6,695,764 B2* | 2/2004 | Silverman et al. ............. 600/29 |
| 6,709,442 B2* | 3/2004 | Miller et al. ................ 606/153 |
| 6,716,222 B2* | 4/2004 | McAlister et al. .......... 606/139 |
| 6,736,828 B1* | 5/2004 | Adams et al. .............. 606/213 |
| 6,746,460 B2 | 6/2004 | Gannoe et al. |
| 6,820,791 B2 | 11/2004 | Adams |
| 6,835,199 B2 | 12/2004 | McGuckin, Jr. et al. |
| 6,840,423 B2 | 1/2005 | Adams et al. |
| 6,921,361 B2* | 7/2005 | Suzuki et al. ................ 600/106 |
| 6,926,722 B2 | 8/2005 | Geitz |
| 6,938,814 B2 | 9/2005 | Sharma et al. |
| 6,966,919 B2 | 11/2005 | Sixto, Jr. et al. |
| 2002/0082621 A1* | 6/2002 | Schurr et al. ................ 606/151 |
| 2002/0111534 A1* | 8/2002 | Suzuki et al. ................ 600/102 |
| 2003/0139752 A1* | 7/2003 | Pasricha et al. ............. 606/139 |

FOREIGN PATENT DOCUMENTS

EP          1114618      7/2001

* cited by examiner

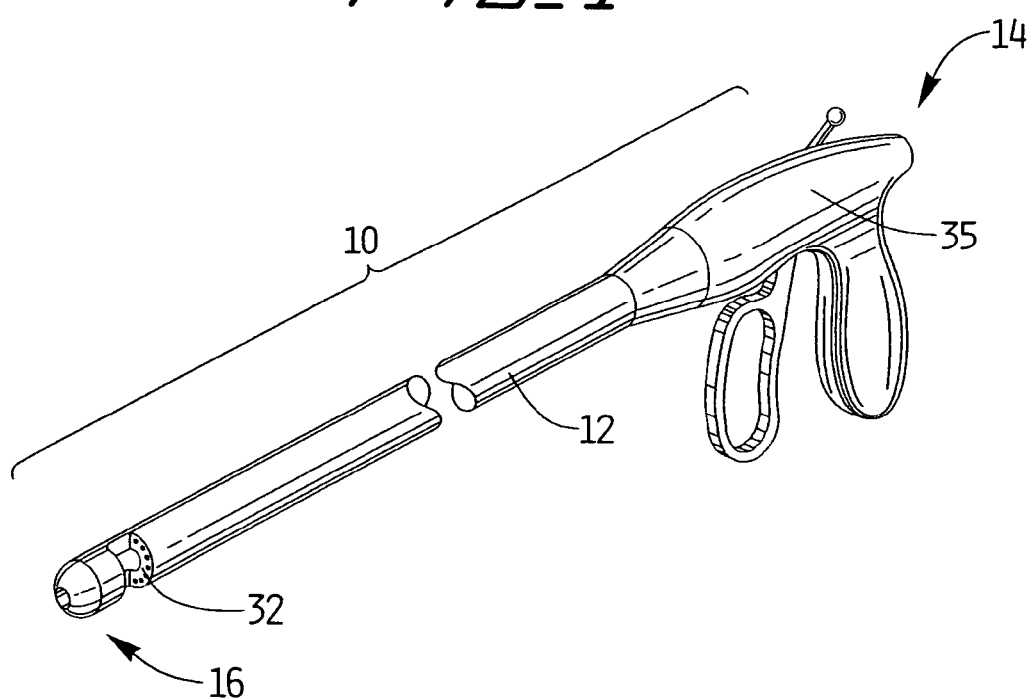
FIG_1
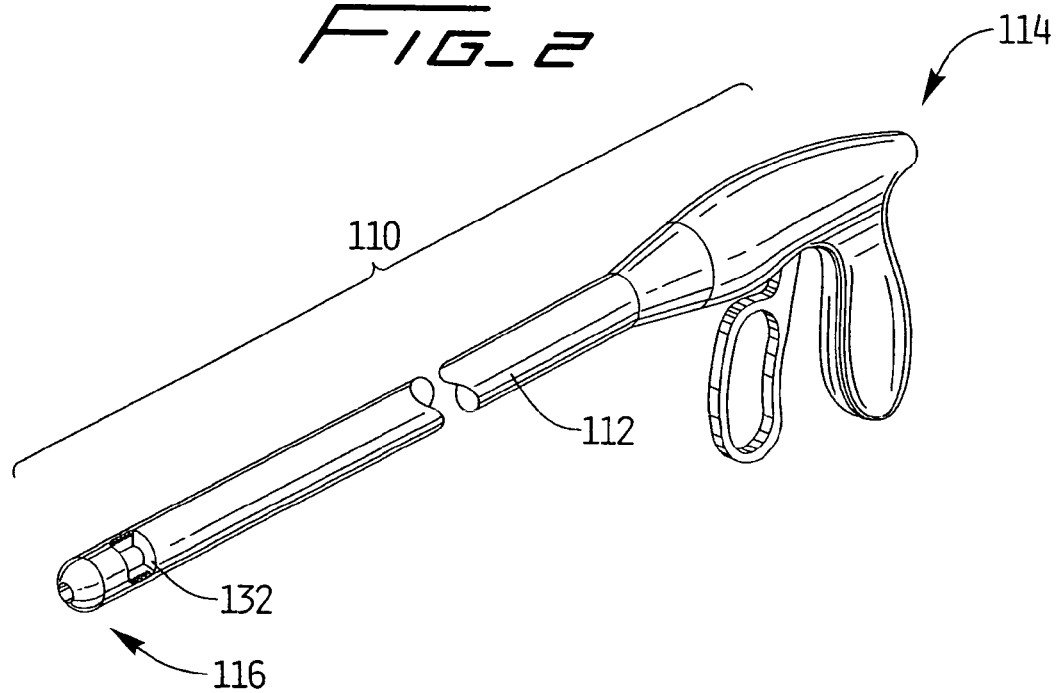
FIG_2

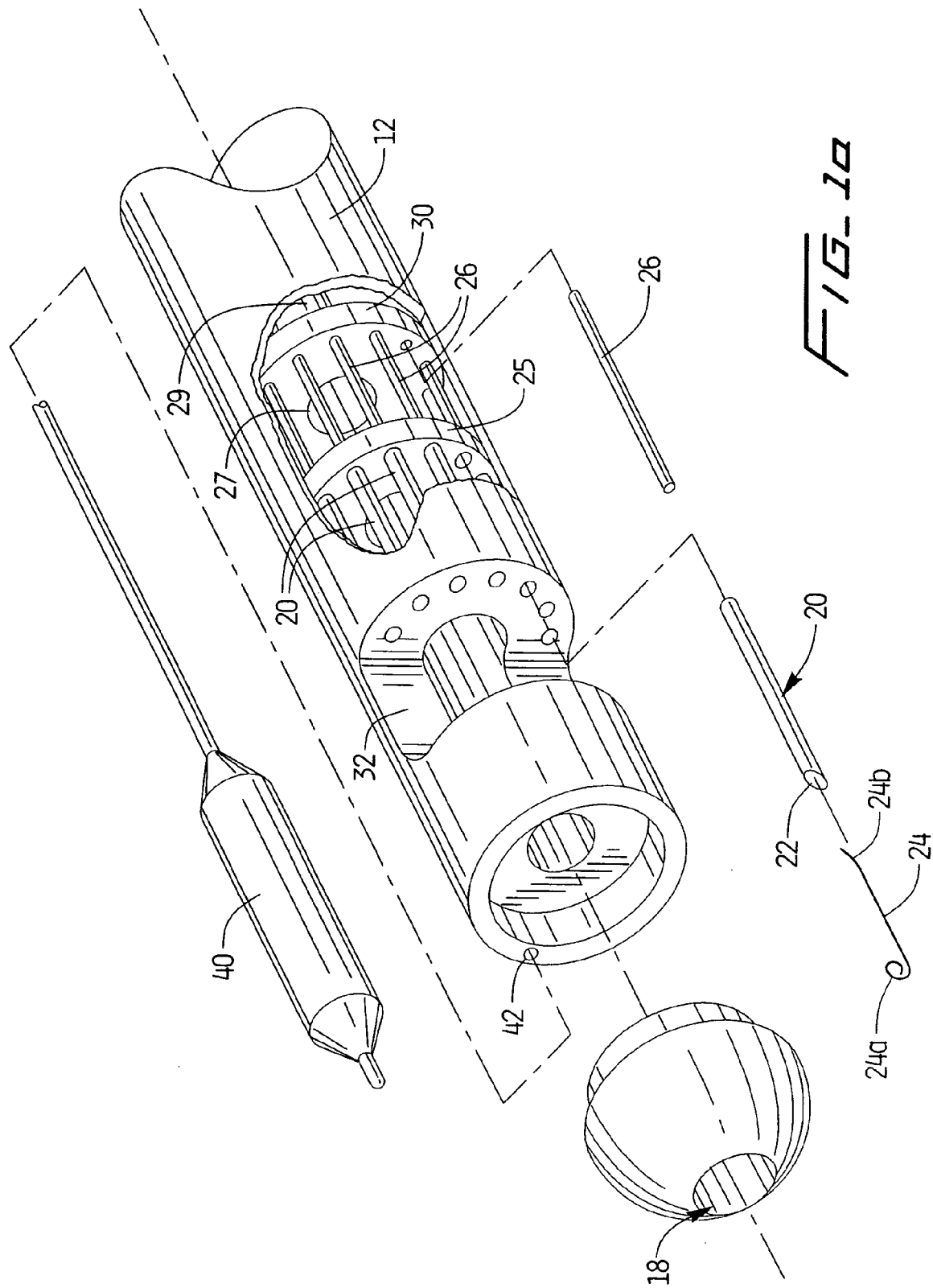

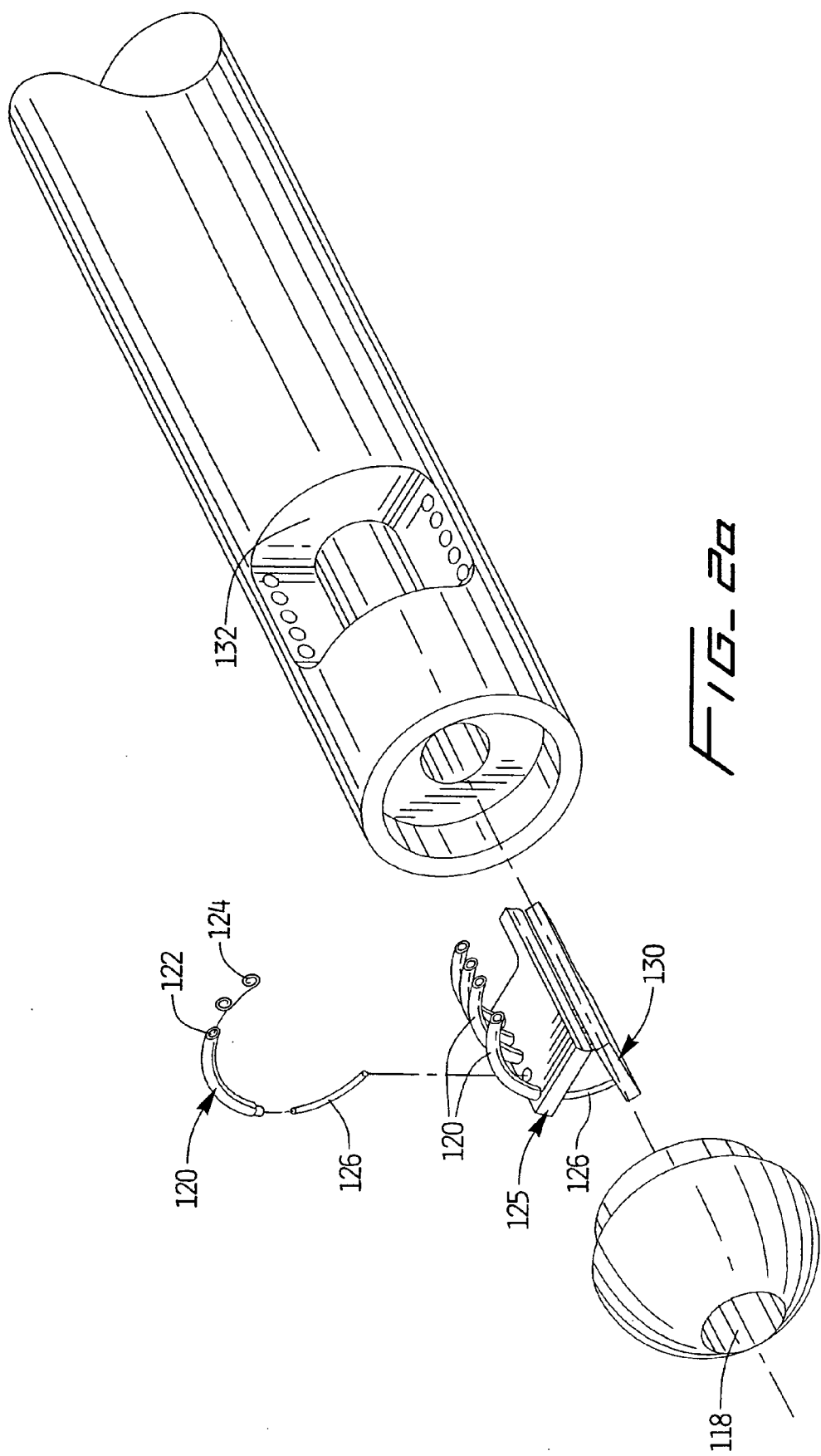

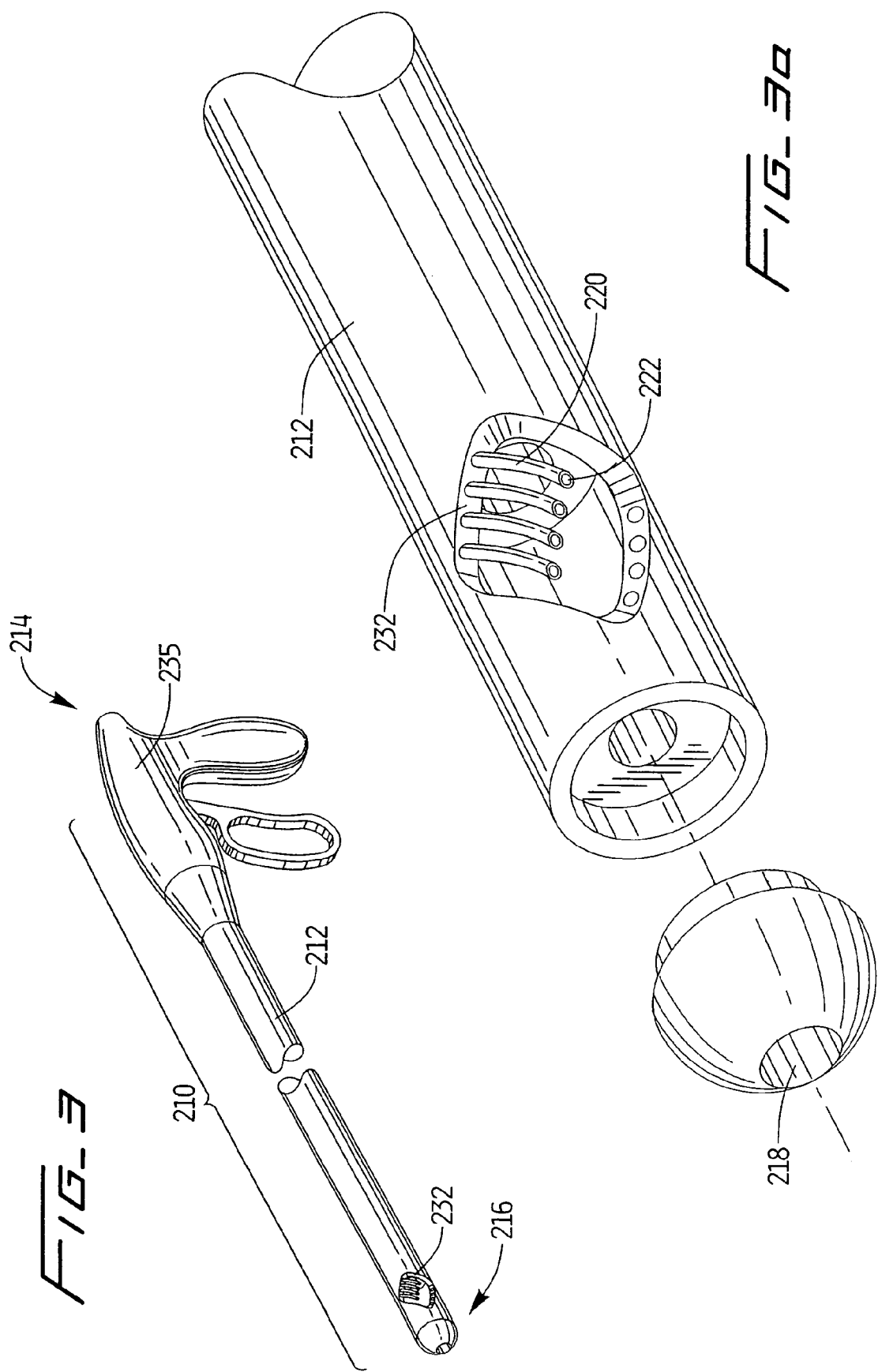

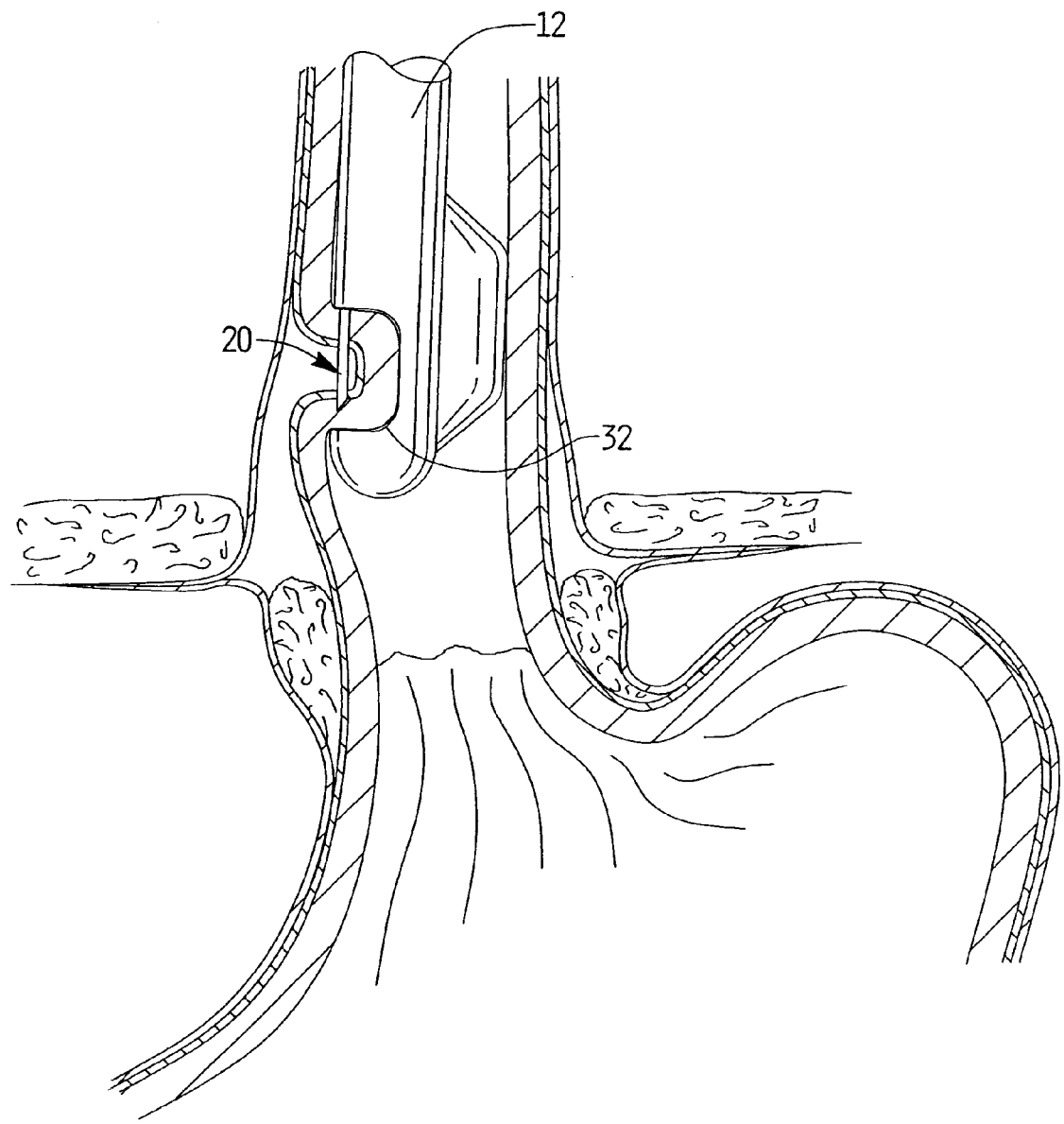
FIG_5

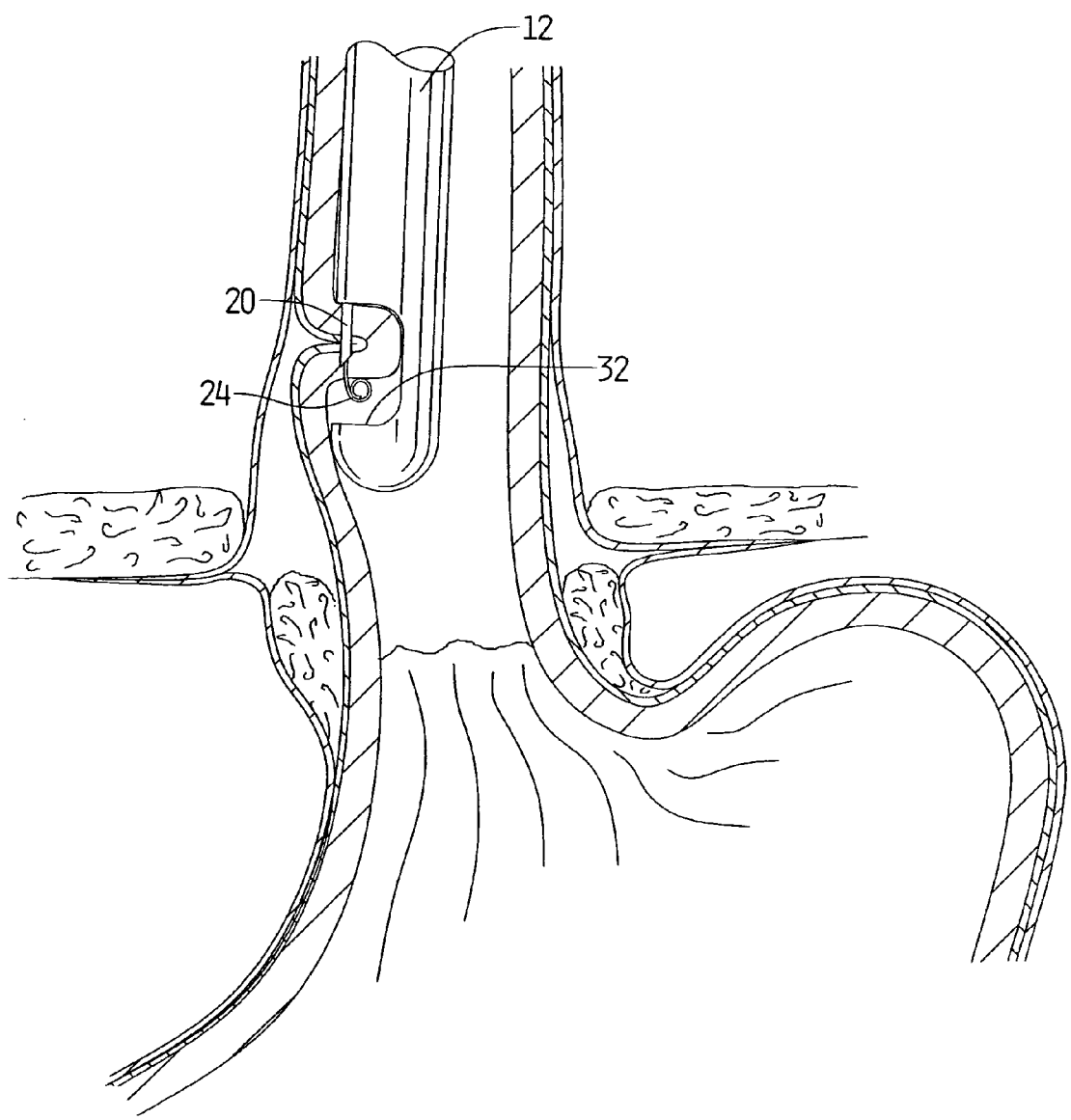
FIG_6

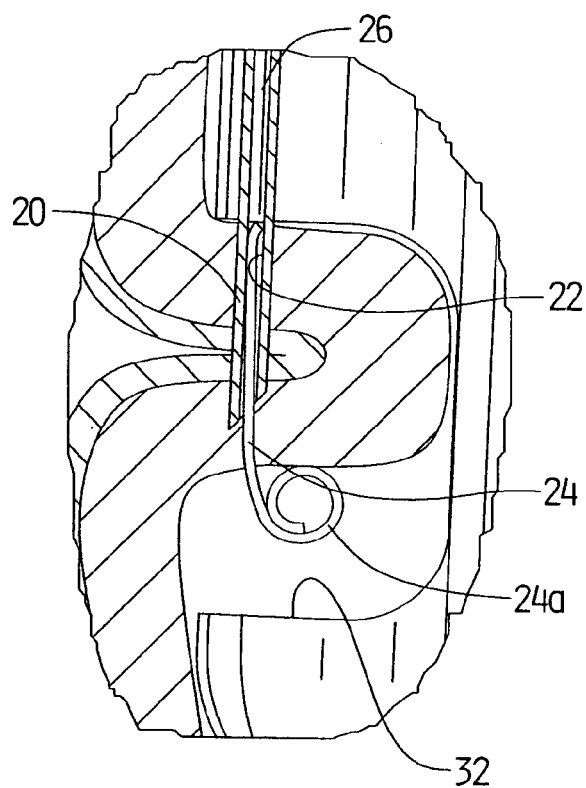
FIG_6a
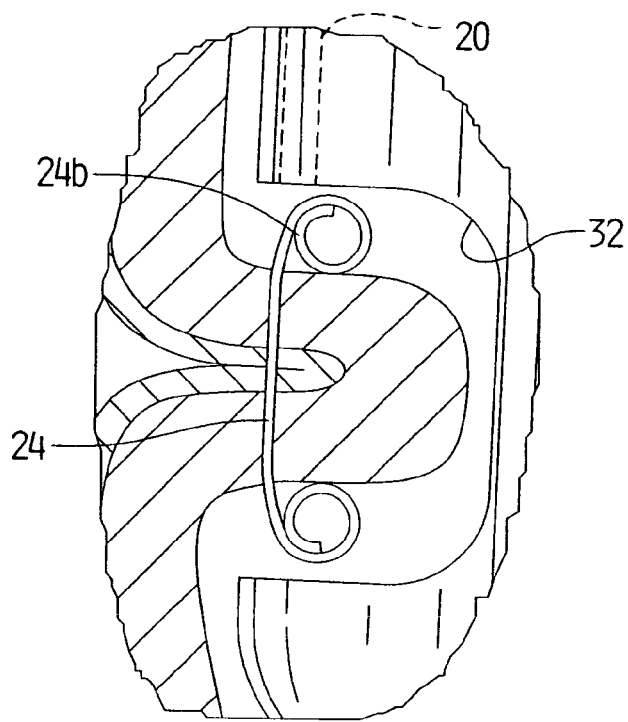
FIG_7a

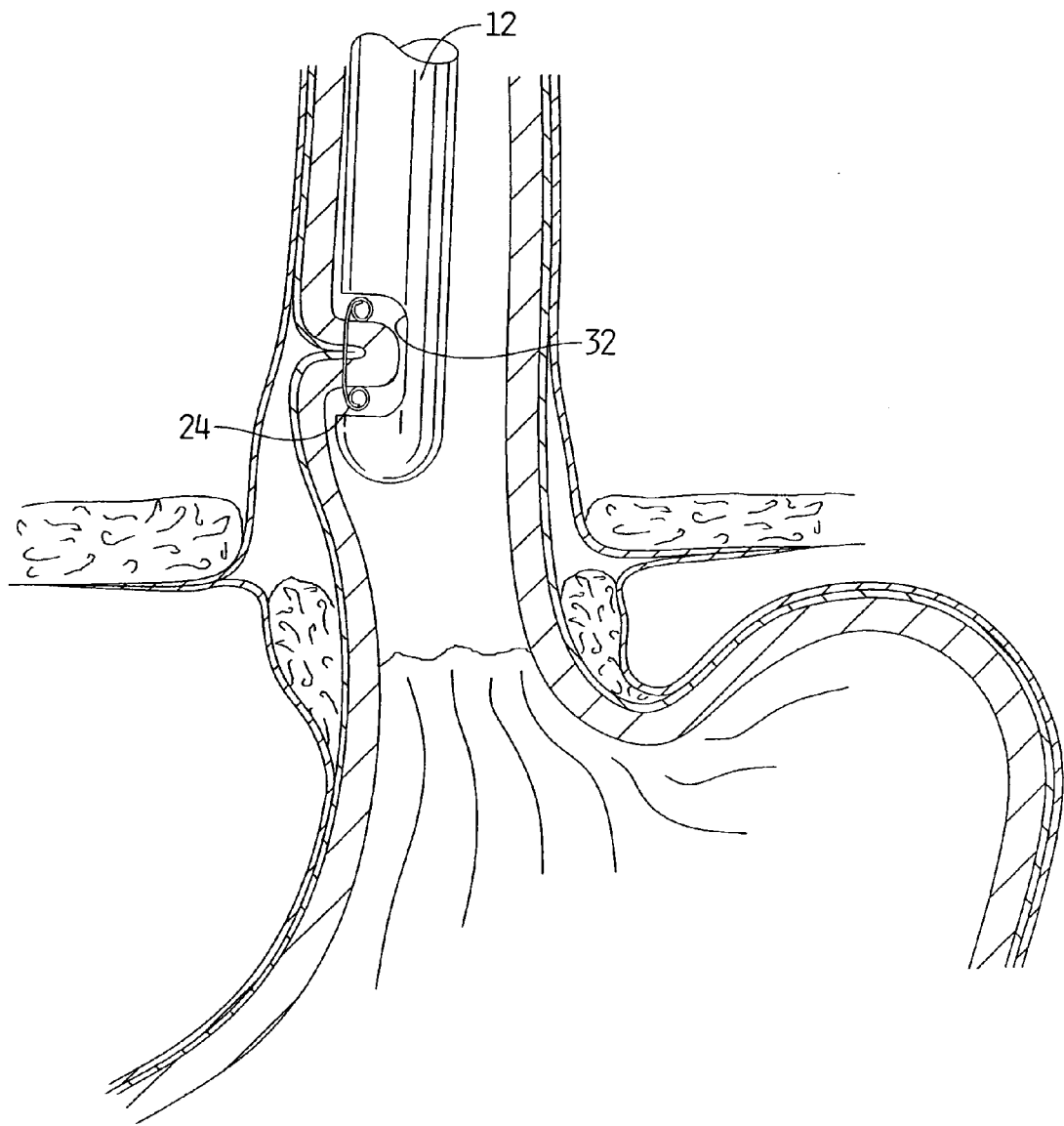
FIG_7

APPARATUS AND METHOD FOR TREATING GASTROESOPHAGEAL REFLUX DISEASE

This application claims priority from provisional application Ser. No. 60/342,540 filed Dec. 20, 2001, the entire content of which are incorporated herein by reference.

BACKGROUND OF THE INVENTION

1. Field of the Invention

The subject invention is directed to a minimally invasive surgical procedure, and more particularly, to an endoscopic surgical procedure for treating gastroesophageal reflux disease, and apparatus for performing the procedure.

2. Background of the Related Art

Gastroesophageal reflux disease (GERD) is one of the most common upper-gastrointestinal disorders in the western world, with a prevalence of approximately 360 cases per 100,000 population per year. Approximately 25 will eventually have recurrent, progressive disease and are candidates to undergo anti-reflux surgical procedures for effective long term therapy.

GERD is a condition in which acids surge upward from the stomach into the esophagus. Backflow of acid into the esophagus makes it raw, red and inflamed, producing the condition known as esophagitis; it also causes the painful, burning sensation behind the breastbone known as heartburn. Backflow or reflux of acid can occur when the sphincter or band muscle at the lower end of the esophagus fails to stay closed. This sphincter is called the lower esophageal sphincter (LES). The LES acts as a valve to the stomach, remaining closed until the action of swallowing forces the valve open to allow food to pass from the esophagus to the stomach. Normally the valve closes immediately after swallowing to prevent stomach contents from surging upward. When the LES fails to provide that closure, stomach acids reflux back into the esophagus, causing heartburn.

The general approach for corrective surgery involves creating a new valve or tightening the existing valve. This procedure is known as "fundoplication" and is used to prevent the back flow of stomach acids into the esophagus. Various fundoplication procedures have been developed to correct GERD and are known as Nissen fundoplication, Belsey Mark IV repair, Hill repair and Dor repair. Each surgical procedure has its own unique attributes; however, each requires an invasive surgical procedure, whereby the individual must endure trauma to the thoracic cavity. The individual remains hospitalized after the procedure for about six to ten days.

The Nissen fundoplication technique involves enveloping the lower esophagus with the gastric fundus by suturing the anterior and posterior fundal folds about the esophagus. Modifications of this procedure include narrowing of the esophageal hiatus posterior to the esophagus, anchoring of the fundoplication to the preaortic fascia and surgical division of the vegus nerve. The degree of the fundal wrap can be modified to incompletely encircle the esophageal tube to avoid gas float syndrome and has also been modified to include a loose wrap. Similarly, the Belsey Mark IV repair, Hill repair and Dor repair are directed to modifications for encirclement of the esophageal tube by fascia.

Complications of these fundoplication procedures include the inability to belch or vomit, dysphagia, gastric ulcer, impaired gastric emptying and slippage of the repair that may foil the best surgical results. Therefore, the fundoplication procedures have been modified to adjust the length and tension of the wrap, include or exclude esophageal muscle in the sutures and leaving the vagus nerves in or out of the encirclement.

A relatively new fundoplication technique is known as Nissen fundoplication laparoscopy. In contrast to the traditional Nissen fundoplication procedure, which requires a 6 to 10 inch incision and a 6 to 10 day hospital stay with up to 8 weeks of recovery at home, the laparoscopy technique is performed through small openings about the abdominal cavity and most patients tend to leave the hospital in two days and can return to work and other activities within a week or two. Despite the benefits of less invasive laparoscopic fundoplication procedures, there is still a need for a minimally invasive corrective treatment for GERD that can be performed on an out-patient basis.

SUMMARY OF THE INVENTION

The subject invention is directed to a new and useful minimally invasive surgical procedure for treating Gastroesophageal reflux disease by reducing the diameter of the esophagus proximate to the lower esophageal sphincter, and to an endoscopic surgical apparatus for performing the procedure. The method includes the steps of forming a fold of esophageal tissue proximate to the lower esophageal sphincter, and extending at least one needle through the fold of esophageal tissue. Each of the needles has an interior lumen containing a tissue fastener. The method further includes the steps of ejecting a distal portion of the tissue fastener from the interior lumen of each needle such that the distal portion of each tissue fastener is disposed against a distal surface of the fold of esophageal tissue, and retracting each needle from the fold of esophageal tissue such that a proximal portion of each tissue fastener is deployed from the interior lumen of each needle and is disposed against a proximal surface of the fold of esophageal tissue.

The method further comprises the step of providing an endoscopic device having a an interior lumen for supporting the needles in a manner that permits the reciprocal movement thereof, and a tissue reception cavity for receiving the fold of esophageal tissue. The method includes guiding the endoscopic device through the esophagus to a location wherein the tissue reception cavity is disposed proximate to the lower esophageal sphincter. Thus, the step of forming the fold of esophageal tissue includes the step of drawing esophageal tissue into the tissue reception cavity of the endoscopic device. This may be accomplished using suction or with a tissue grasping device.

Preferably, a tissue fastener of shape memory alloy or a similar bio-compatible material having memory characteristics is provided within the interior lumen of each needle in a generally elongate orientation. The step of ejecting a tissue fastener from the interior lumen of a needle includes permitting the distal portion of the tissue fastener to move to a normally unstressed condition (at body temperature) wherein the distal portion of the tissue fastener is in a curved or coiled orientation. The step of retracing the needle from the fold of esophageal tissue includes permitting the proximal portion of the tissue fastener to move to a normally unstressed condition (at body temperature) wherein the proximal portion of the tissue fastener is in a curved or coiled orientation. It is envisioned that the needles may be extended through the fold of esophageal tissue simultaneously or in seriatim. Similarly, the tissue fasteners may be ejected from the needles simultaneously or in seriatim. After the fasteners have been ejected from the needles, the fold of esophageal tissue is released from the tissue reception cavity, and the endoscopic device is withdrawn from the esophagus.

The subject invention is further directed to an endoscopic surgical apparatus for performing the method summarized above. The apparatus includes an elongated tubular body having opposed proximal and distal end portions and an interior lumen extending therethrough. An endoscope may be housed within the interior lumen of the tubular body. Preferably, one or more needles are disposed within the elongated tubular body and are mounted for reciprocal movement therein between a retracted position and a protracted position. Depending upon the configuration and orientation of the needles within the tubular body, it is envisioned that the reciprocal movement thereof may be either longitudinal, rotational or helical. Each of the needles has an interior lumen extending therethrough. A tissue fastener is disposed within the interior lumen of each needle. The fasteners are configured for movement between an initially straight position within the interior lumen of a needle and a subsequently coiled or curved position ejected from the interior lumen of a needle.

A mechanism is provided for effectuating reciprocal movement of the needle within the interior bore of the elongated tubular body, and a mechanism if provided for ejecting the tissue fasteners from the interior lumen of the needles. Preferably, a tissue receiving window is formed within the distal end portion of the elongated tubular body for receiving a fold of esophageal tissue. Thus, the retracted position of the needle is proximal to or, in some instances lateral to the tissue receiving window and the protracted position of the needle is distal of the tissue receiving window.

These and other aspects of the subject invention and the method of using the same will become more readily apparent to those having ordinary skill in the art from the following detailed description of the invention taken in conjunction with the drawings described hereinbelow.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIG. 1 is a perspective view of a surgical apparatus constructed in accordance with a preferred embodiment of the subject invention;

FIG. 1a is an enlarged localized perspective view, in partial cross-section, of the distal portion of the surgical apparatus of FIG. 1, with parts separated for ease of illustration, wherein the apparatus includes a plurality of elongated needles mounted for reciprocal longitudinal movement relative to the longitudinal axis of the apparatus;

FIG. 2 is a perspective view of another surgical apparatus constructed in accordance with a preferred embodiment of the subject invention;

FIG. 2a is an enlarged localized perspective view of the distal portion of the surgical apparatus of FIG. 2, with parts separated for ease of illustration, wherein the apparatus includes a plurality of curved needles mounted for reciprocal rotational movement relative to the longitudinal axis of the apparatus;

FIG. 3 is a perspective view of another surgical apparatus constructed in accordance with a preferred embodiment of the subject invention;

FIG. 3a is an enlarged localized perspective view of the distal portion of the surgical apparatus of FIG. 3, with parts separated for ease of illustration, wherein the apparatus includes a plurality of partially helical needles mounted for reciprocal helical movement relative to the longitudinal axis of the apparatus;

FIG. 5 is a side elevational view the distal portion of the surgical apparatus of FIG. 1 illustrating the extension of a needle through the fold of esophageal tissue, wherein the interior lumen of the needle contains a tissue fastener;

FIG. 6 is a side elevational view the distal portion of the surgical apparatus of FIG. 1 illustrating the ejection of a distal portion of the tissue fastener from the interior lumen of the needle such that the distal portion of the tissue fastener is disposed against a distal surface of the fold of esophageal tissue;

FIG. 6a is an enlarged localized view of the needle shown in FIG. 6 illustrating the ejection of the fastener from the interior lumen of the needle by the needle pusher;

FIG. 7 is a side elevational view of the distal portion of the surgical apparatus of FIG. 1 illustrating the retraction of the needle from the fold of esophageal tissue such that a proximal portion of tissue fastener is deployed from the interior lumen of the needle and is disposed against a proximal surface of the fold of esophageal tissue; and FIG. 7a is an enlarged localized view of the needle shown in FIG. 7 illustrating the retraction of the needle from the fold of tissue.

DETAILED DESCRIPTION OF PREFERRED EMBODIMENTS

Figure 4:
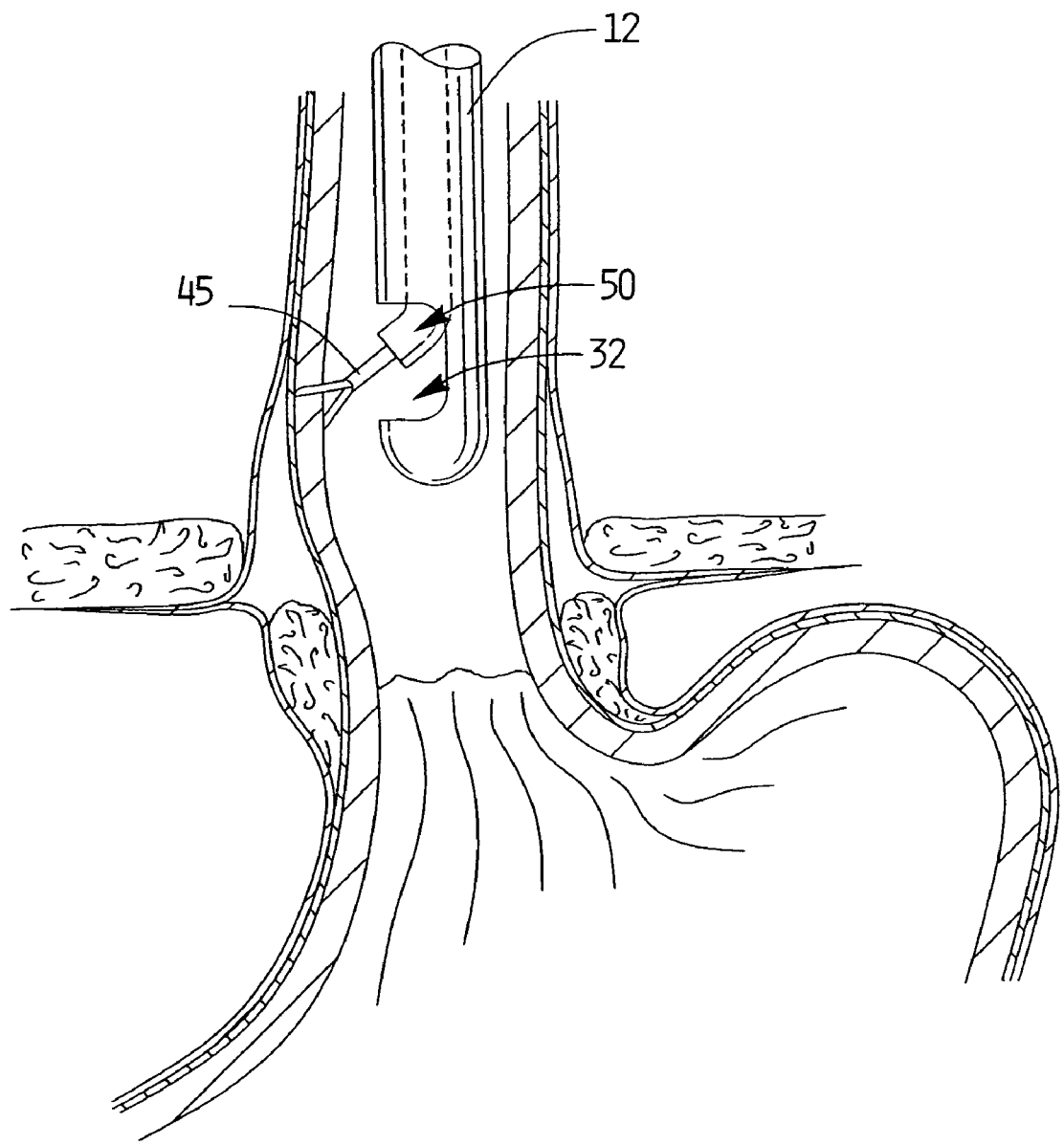
FIG. 4 is a side elevational view of the distal portion of the surgical apparatus of FIG. 1 illustrating the formation of a fold of esophageal tissue proximate to the lower esophageal sphincter during a treatment procedure.

Referring now to the drawings wherein like reference numerals identify similar structural features of the apparatus disclosed herein, there is illustrated in FIG. 1 an endoscopic surgical apparatus constructed in accordance with a preferred embodiment of the subject invention and designated generally by reference numeral 10.

Referring to FIG. 1 in conjunction with FIG. 1a, endoscopic surgical apparatus 10 includes an elongated flexible tubular body 12 having opposed proximal and distal end portions 14, 16 and an interior lumen 18 extending therethrough. Elongated flexible needles 20 with tapered leading edges are disposed within the elongated tubular body 12 and are mounted for reciprocal longitudinal movement therein between a retracted position and a protracted position. More particularly, the elongated needles 20 are supported in circumferentially spaced relationship within tubular body 12 by a needle block 25. Needle block 25 is mounted at the distal end of a tubular drive shaft 27 which is adapted for reciprocal axial movement within tubular body 12.

Each elongated needle 20 has an interior lumen 22 extending therethrough. A tissue fastener 24 formed of a shape memory metal alloy, such as a nickel-titanium alloy, is disposed within the interior lumen of each needle 20. The tissue fastener 24 is configured for movement between an initially straight position within the interior lumen of the elongated needle and a subsequently coiled position ejected from the interior lumen of the elongated needle. In the straight position, and in the coiled position, opposed end portions 24a, 24b of the fastener 24 have a generally curved configuration. In FIG. 2a, the end portion 24a of fastener 24 is shown in the coiled position, while the opposed end portion 24b is shown in a transitional state between the initially straight position and the subsequently coiled or curved position.

An elongated push rod 26 extends through the interior lumen 22 of each elongated needle 20 for ejecting at least a portion of the tissue fastener 24 from the interior lumen 22 of the elongated needle 20. Each push rod 26 is supported in circumferentially spaced relationship by a push rod block 30. Push rod block 30 is mounted at the distal end of a tubular drive shaft 29 which is mounted coaxial with drive shaft 27. Drive shaft 29 is adapted and configured for reciprocal axial motion within tubular body 12.

As best seen in FIG. 1, surgical apparatus 10 further includes an actuation mechanism 35 operatively associated with a proximal portion 14 of the elongate body 12. Actuation mechanism 35 is adapted and configured to effectuate reciprocal longitudinal movement of the drive shaft 27 associated with needle block 25 and the drive shaft 29 associated with push rod block 30. It is envisioned that actuation mechanism 35 can take the form of a mechanical actuator, a pneumatic actuator, a hydraulic actuator or an electrical actuator which transmits force to the drive shafts 27, 29 through conventional mechanisms, such as cooperative linkages, gear trains or combinations thereof. It is also envisioned that the fasteners can be fired in a proximal direction.

Surgical apparatus 10 further includes a generally U-shaped or concave tissue receiving window 32 formed within the distal end portion of the elongated tubular body 12. In the retracted position, the elongated needles 20 are proximal of the tissue receiving window 32 and in the protracted position, the elongated needles 22 travel to a position that is distal to the tissue receiving window 32.

As illustrated in FIG. 1a, as an option, the surgical apparatus 10 of the subject invention could be provided with an angioplasty balloon 40 that would be accommodated within an elongated lateral lumen 42. It is envisioned that angioplasty balloon 40 could be extended from the distal end of tubular body 12 and used as a dilator to increase the esophageal diameter prior to placement of the fasteners 24.

Referring to FIGS. 2 and 2a, there is illustrated another surgical apparatus 110 constructed in accordance with a preferred embodiment of the subject invention that includes an elongated body 112 having opposed proximal and distal end portions 114 and 116, and an interior lumen 118 extending therethrough. The distal end portion 116 has a tissue receiving window 132 formed therein and the proximal portion 114 has an actuator handle 135 operatively associated therewith.

As best seen in FIG. 2a, surgical apparatus 110 includes a plurality of curved needles 120 each supporting a surgical fasteners 124 in the interior lumen 122 thereof. The curved needles 120 are supported in axially spaced relationship on a needle block 125 that is mounted for reciprocal rotational movement within body portion 112. A plurality of curved push rods 126 are supported on a push rod block 130 adjacent needle block 125. Each push rod 126 is configured to eject at least a portion of a tissue fastener 124 from the interior lumen 122 of a needle 120 upon actuation of handle 135. Those skilled in the art will readily appreciate that conventional mechanisms such as drive screws or drive shafts may be employed to transmit rotational motion from actuation handle 135 to needle block 125 and push rod block 130.

Referring to FIGS. 3 and 3a, there is illustrated another surgical apparatus 210 constructed in accordance with a preferred embodiment of the subject invention that includes an elongated body 212 having opposed proximal and distal end portions 214 and 216, and an interior lumen 218. A tissue receiving window 232 is formed in the distal end portion 216 and an actuator handle 235 is operatively associated with the proximal potion 214. As best seen in FIG. 3a, surgical apparatus 210 differs from surgical apparatus 110 in that it includes a plurality of partially helical needles 220 that are mounted for reciprocal helical movement within body portion 212 relative to the longitudinal axis of body portion 212.

While not shown in FIG. 3a, a surgical fastener formed from shape memory alloy is supported with the interior lumen 222 of each needle 220 and is configured for deployment in the manner described above with respect to apparatus 110. Those skilled in the art will readily appreciate that conventional mechanisms such as drive screws or drive shafts may be employed to transmit helical motion from actuation handle 235 to the needle block and push rod block operatively associated with curved needles 220.

The subject invention is also directed to a method of treating gastroesophageal reflux disease using a surgical apparatus constructed in accordance a preferred embodiment of the subject invention, such as, for example, surgical apparatus 10. Initially, during a surgical procedure, the elongated body 12 of surgical apparatus 10 is extended through the esophagus such that tissue receiving window 32 is positioned in a location that is proximate to the esophageal sphincter. Next, as shown in FIG. 4, a fold of esophageal tissue is drawn into the tissue receiving window 32. This is preferably done under visual observation using the flexible endoscope 50 extended through the interior lumen 18 of body 12, and is preferably accomplished by suction or using a tissue grasping device such as tissue grasper 45.

Thereafter, one or more needles 20 are extended through the fold of esophageal tissue, as shown in FIG. 5. At such a time, the distal portion 24a of the tissue fastener 24 in each needle 20 is ejected from the interior lumen 22 of each needle 20 by push rod 26 such that the distal portion 24a of each tissue fastener 24 is disposed against a distal surface of the fold of esophageal tissue in a curved condition, as shown in FIGS. 6 and 6a. Then, as shown in FIGS. 7 and 7a, needles 20 are retracted from the fold of esophageal tissue such that the proximal portion 24b of each tissue fastener 24 is deployed from the interior lumen 22 of needle 20 and is disposed against a proximal surface of the fold of esophageal tissue.

In instances wherein more than one needle is employed, the needles may be extended through the fold of esophageal tissue either simultaneously or in seriatim by staging the needles at different positions relative to one another. Similarly, the tissue fasteners may be ejected from the needles simultaneously or in seriatim by staging the push rods at different positions relative to one another. After the needles have been retracted, the fold of esophageal tissue is released from the tissue reception cavity.

Once the fasteners 24 have been deployed, the fold of tissue with which they are associated will undergo repetitive movement during peristalsis. Since the ends of the fasteners are curved and flexible, they will advantageously comply with the fold of tissue as it moves. This flexibility also accommodates belching and vomiting. Furthermore, the flexible configuration of the fasteners facilitates the easy removal thereof from the fold of tissue should it become necessary to reverse the procedure. This may be done with a grasping device, such as that which is illustrated in FIG. 4.

Preferably, the steps of the subject invention are performed under vision using an endoscope which may be provided integral with surgical device 10. Alternatively, the treatment method of the subject invention may be performed using either ultrasound, fluoroscopy or magnetic resonance imaging.

It is also envisioned and well within the scope of the subject invention that the surgical apparatus 10 and the method of using the same can be employed to reduce the volume of a patients stomach. In such a procedure, gastric tissue would be fastened using the apparatus of the subject invention. Since the ends of the fasteners utilized in this procedure are curved and flexible, they will comply or unfurl with the fold of tissue as the stomach expands with the intake of food.

Although the apparatus and method of the subject invention have been described with respect to preferred embodiments, those skilled in the art will readily appreciate that changes and modifications may be made thereto without departing from the spirit and scope of the present invention as defined by the appended claims.

What is claimed is:

1. A method of treating gastroesophageal reflux disease comprising the steps of:
   a) forming a fold of esophageal tissue proximate to the lower esophageal sphincter and drawing the fold of esophageal tissue into a tissue receiving cavity formed in an apparatus;
   b) actuating a mechanism to make contact with and extend a plurality of needles from the apparatus through the fold of esophageal tissue such that the needles travel through the tissue receiving cavity of the apparatus, the plurality of needles having an interior lumen containing a tissue fastener;
   c) ejecting a distal portion of the tissue fasteners from the interior lumen of the needle such that the distal portion of the tissue fasteners are disposed against a distal surface of the fold of esophageal tissue and the distal portion moves to a curved configuration; and
   d) retracting the needles from the fold of esophageal tissue such that a proximal portion of the tissue fasteners deployed from the respective interior lumen of the needles and are disposed against a proximal surface of the fold of esophageal tissue to thereby fasten the tissue to leave the fold therein to reduce the diameter of a patient's esophagus proximate the lower esophageal sphincter by the presence of the fold;
   wherein the plurality of needles are axially spaced within the apparatus and a distal tip of the needles is transverse to a longitudinal axis of the apparatus, and the step of actuating a mechanism to extend the plurality of needles comprises extending the needles in a rotational movement.

2. A method according to claim 1, further comprising the step of providing an endoscopic device, the endoscopic device having the tissue reception cavity formed in a distal end portion.

3. A method according to claim 2, wherein the step of drawing esophageal tissue into the tissue reception cavity of the endoscopic device is performed under suction.

4. A method according to claim 2, wherein the step of drawing esophageal tissue into the tissue reception cavity of the endoscopic device is performed with a tissue grasping device.

5. A method according to claim 2, further comprising the step of guiding the endoscopic device through the esophagus to a location wherein the tissue reception cavity is disposed proximate to the lower esophageal sphincter.

6. A method according to claim 2, further comprising the step of providing the needles within an interior lumen of the endoscopic device.

7. A method according to claim 6, further comprising the step of providing the tissue fasteners within the interior lumen of the needles in an initial condition wherein the fasteners are in a generally elongate orientation and wherein the step of ejecting the fasteners from the interior lumen of the needles includes permitting the distal portion of the tissue fasteners to move to a normal condition wherein the distal portion of the tissue fasteners are in the curved orientation.

8. A method according to claim 7, wherein the step of retracting the needles from the fold of esophageal tissue includes permitting the proximal portion of the tissue fasteners to move to a normal condition wherein the proximal portion of the tissue fasteners are in a curved orientation.

9. A method according to claim 1, further comprising the step of providing an endoscope for performing the steps of the method under vision.

10. A method according to claim 9, wherein the endoscope is provided as an integral part of the endoscopic device.

11. A method according to claim 10, wherein the needles are extended through the fold of esophageal tissue simultaneously and the tissue fasteners are ejected from the needles simultaneously.

12. A method according to claim 2, wherein the needles are extended through the fold of esophageal tissue in seriatim and the tissue fasteners are ejected from the needles in seriatim.

* * * * *